US008968776B2

(12) United States Patent
Seth et al.

(10) Patent No.: US 8,968,776 B2
(45) Date of Patent: Mar. 3, 2015

(54) COMPOSITION COMPRISING A BENZIMIDAZOLE AND PROCESS FOR ITS MANUFACTURE

(71) Applicants: Pawan Seth, Irvine, CA (US); Benoît Schmitt, Irvine, CA (US)

(72) Inventors: Pawan Seth, Irvine, CA (US); Benoît Schmitt, Irvine, CA (US)

(73) Assignee: UCB, Inc., Smyrna, GA (US)

( * ) Notice: Subject to any disclaimer, the term of this patent is extended or adjusted under 35 U.S.C. 154(b) by 0 days.

(21) Appl. No.: 13/895,492

(22) Filed: May 16, 2013

(65) Prior Publication Data

US 2013/0251791 A1 Sep. 26, 2013

Related U.S. Application Data

(63) Continuation of application No. 10/901,898, filed on Jul. 29, 2004, now abandoned.

(51) Int. Cl.
*A61K 9/20* (2006.01)
*A61K 9/50* (2006.01)
*A61K 9/28* (2006.01)
*A61K 31/4184* (2006.01)
*A61K 31/4439* (2006.01)

(52) U.S. Cl.
CPC ............. *A61K 9/5073* (2013.01); *A61K 9/2846* (2013.01); *A61K 9/2866* (2013.01); *A61K 9/2886* (2013.01); *A61K 31/4184* (2013.01); *A61K 9/2081* (2013.01); *A61K 31/4439* (2013.01)
USPC ........... 424/464; 424/465; 424/469; 424/474; 424/489; 424/490

(58) Field of Classification Search
None
See application file for complete search history.

(56) References Cited

U.S. PATENT DOCUMENTS

| | | | |
|---|---|---|---|
| 4,045,563 A | 8/1977 | Berntsson et al. ............. 424/263 |
| 4,182,766 A | 1/1980 | Krassó et al. ................. 424/263 |
| 4,255,431 A | 3/1981 | Junggren et al. .............. 424/263 |
| 4,337,257 A | 6/1982 | Junggren et al. .............. 424/263 |
| 4,472,409 A | 9/1984 | Senn-Bilfinger ............. 424/263 |
| 4,508,905 A | 4/1985 | Junggren et al. .............. 546/271 |
| 4,555,518 A | 11/1985 | Rainer ........................ 514/338 |
| 4,560,693 A | 12/1985 | Rainer ........................ 514/338 |
| 4,628,098 A | 12/1986 | Nohara et al. ................ 546/271 |
| 4,689,333 A | 8/1987 | Nohara et al. ................ 514/338 |
| 4,721,709 A | 1/1988 | Seth et al. .................... 514/221 |
| 4,734,416 A | 3/1988 | Banno et al. ................. 514/253 |
| 4,738,974 A | 4/1988 | Brändström ................ 514/338 |
| 4,758,579 A | 7/1988 | Kohl et al. .................... 514/338 |
| 4,786,505 A | 11/1988 | Lovgren et al. .............. 424/468 |
| 4,795,643 A | 1/1989 | Seth ............................ 424/456 |
| 4,844,903 A | 7/1989 | Seth ............................ 424/448 |
| 4,853,230 A | 8/1989 | Lovgren et al. .............. 424/466 |
| 5,006,528 A | 4/1991 | Oshiro et al. ................ 514/253 |
| 5,013,743 A | 5/1991 | Iwahi et al. .................. 514/338 |
| 5,026,560 A | 6/1991 | Makino et al. ............... 424/494 |
| 5,035,899 A | 7/1991 | Saeki et al. .................. 424/480 |
| 5,039,806 A | 8/1991 | Brändström et al. .......... 546/271 |
| 5,045,321 A | 9/1991 | Makino et al. ............... 424/475 |
| 5,045,552 A | 9/1991 | Souda et al. ................ 514/338 |
| 5,093,132 A | 3/1992 | Makino et al. ............... 424/475 |
| 5,433,959 A | 7/1995 | Makino et al. ............... 424/475 |
| 5,690,960 A | 11/1997 | Bengtsson et al. ............ 424/480 |
| 5,693,818 A | 12/1997 | Von Unge ................ 546/273.7 |
| 5,714,504 A | 2/1998 | Lindberg et al. ............. 514/338 |
| 5,817,338 A | 10/1998 | Bergstrand et al. ........... 424/468 |
| 5,824,341 A | 10/1998 | Seth et al. .................... 424/473 |
| 5,877,192 A | 3/1999 | Lindberg et al. ............. 514/338 |
| 5,900,424 A | 5/1999 | Källström et al. ............. 514/338 |
| 5,997,903 A | 12/1999 | Dietrich et al. ............... 424/482 |
| 6,033,686 A | 3/2000 | Seth ............................ 424/482 |
| 6,048,547 A | 4/2000 | Seth et al. .................... 424/464 |
| 6,074,670 A | 6/2000 | Stamm et al. ................ 424/462 |
| 6,096,341 A | 8/2000 | Seth ............................ 424/482 |
| 6,117,453 A | 9/2000 | Seth et al. .................... 424/486 |
| 6,143,327 A | 11/2000 | Seth ............................ 424/482 |
| 6,147,103 A | 11/2000 | Anousis et al. ............... 514/394 |
| 6,150,380 A | 11/2000 | Lövqvist ..................... 514/338 |
| 6,159,499 A | 12/2000 | Seth ............................ 424/451 |
| 6,166,213 A | 12/2000 | Anousis et al. ............ 546/273.7 |
| 6,191,148 B1 | 2/2001 | McManus et al. ............ 514/341 |
| 6,207,198 B1 | 3/2001 | Seth ............................ 424/494 |
| 6,248,355 B1 | 6/2001 | Seth ............................ 424/458 |

(Continued)

FOREIGN PATENT DOCUMENTS

| | | | | |
|---|---|---|---|---|
| DE | 3415971 | 11/1984 | ......... | C07D 401/12 |
| EP | 0005129 | 10/1979 | ......... | C07D 403/12 |

(Continued)

OTHER PUBLICATIONS

*AstraZeneca AB, et al.* v. *Mylan Laboratories, Inc. et al.* (S.D.N.Y.; No. 00-CIV-4541, 03-CIV-8719; before Judge B.S. Jones), Astra's Proposed Findings of Fact for Infringement, Section I, pp. 13-15; Section II, pp. 11-12, Section III, pp. 3-7; Section IV, pp. 2-3.

Melia, C.D. et al. (1989), Review article; mechanisms of drug release from tablets and capsules. I: disintegration, *Aliment. PharmacoL Therap.* 3: 223-232.

NG Industries product description of Sodium Starch Glycolate http://www.nbent.com/SSG.htm (May 9, 2013).

Office action dated Aug. 4, 2006 issued in U.S. Appl. No. 10/901,898.

Office action dated Feb. 15, 2007 issued in U.S. Appl. No. 10/901,898.

(Continued)

*Primary Examiner* — James Rogers
(74) *Attorney, Agent, or Firm* — Florek & Endres, PLLC

(57) ABSTRACT

The invention provides new benzimidazole compositions, comprising: (a) a core containing said benzimidazole active ingredient; (b) an intermediate layer; and (c) an enteric layer; said core being substantially free of binder. The invention also provides a process for manufacturing the composition of the invention.

7 Claims, No Drawings

(56) References Cited

U.S. PATENT DOCUMENTS

| | | | |
|---|---|---|---|
| 6,277,405 B1 | 8/2001 | Stamm et al. | 424/462 |
| 6,338,857 B1 | 1/2002 | Seth | 424/464 |
| 6,348,469 B1 | 2/2002 | Seth | 514/255 |
| 6,350,471 B1 | 2/2002 | Seth | 424/480 |
| 6,368,628 B1 | 4/2002 | Seth | 424/480 |
| 6,369,085 B1 | 4/2002 | Cotton et al. | 514/338 |
| 6,428,810 B1 | 8/2002 | Bergstrand et al. | 424/480 |
| 6,531,153 B2 | 3/2003 | Seth | 424/486 |
| 6,589,552 B2 | 7/2003 | Stamm et al. | 424/457 |
| 6,596,317 B2 | 7/2003 | Stamm et al. | 424/489 |
| 6,652,881 B2 | 11/2003 | Stamm et al. | 424/462 |
| 2002/0009496 A1 | 1/2002 | Stamm et al. | 424/490 |
| 2003/0003151 A1 | 1/2003 | Chopra | 424/473 |
| 2003/0035834 A1 | 2/2003 | Seth | 424/468 |
| 2003/0059466 A1 | 3/2003 | Seth | 424/474 |
| 2003/0091634 A1 | 5/2003 | Seth | 424/468 |
| 2003/0104060 A1 | 6/2003 | Stamm et al. | 424/469 |
| 2003/0114494 A1 | 6/2003 | Schmitt | 514/338 |
| 2003/0118647 A1 | 6/2003 | Seth | 424/468 |
| 2003/0170302 A1 | 9/2003 | Seth et al. | 424/468 |
| 2004/0057997 A1 | 3/2004 | Stamm et al. | 424/468 |
| 2004/0057998 A1 | 3/2004 | Stamm et al. | 424/468 |
| 2004/0057999 A1 | 3/2004 | Stamm et al. | 424/468 |
| 2004/0058005 A1 | 3/2004 | Stamm et al. | 424/489 |
| 2004/0086567 A1 | 5/2004 | Seth | 424/486 |
| 2004/0092597 A1 | 5/2004 | Stamm et al. | 514/571 |
| 2004/0161461 A1 | 8/2004 | Seth et al. | 424/471 |
| 2004/0162320 A1 | 8/2004 | Seth | 514/355 |
| 2004/0176465 A1 | 9/2004 | Seth | 514/649 |
| 2004/0224949 A1 | 11/2004 | Pawan et al. | 514/237.5 |
| 2005/0214372 A1 | 9/2005 | Di Capua et al. | 424/472 |
| 2006/0024362 A1 | 2/2006 | Seth | 424/464 |

FOREIGN PATENT DOCUMENTS

| | | | |
|---|---|---|---|
| EP | 0080602 | 6/1983 | C07D 401/12 |
| EP | 0127763 | 12/1984 | C07D 491/056 |
| EP | 0130729 | 1/1985 | C07D 491/052 |
| EP | 0134400 | 3/1985 | C07D 401/12 |
| EP | 0146370 | 6/1985 | C07D 471/06 |
| EP | 0150586 | 8/1985 | C07D 401/12 |
| EP | 0159144 | 10/1985 | B63H 25/42 |
| EP | 0166287 | 1/1986 | C07D 401/12 |
| EP | 0173664 | 3/1986 | C07D 213/26 |
| EP | 0244380 | 11/1987 | A61K 9/32 |
| GB | 2082580 | 3/1982 | C07D 235/02 |
| GB | 2141429 | 12/1984 | C07D 513/04 |
| GB | 2163747 | 3/1986 | C07D 235/28 |
| WO | WO 97/12581 | 4/1997 | |
| WO | WO 02/45694 | 6/2002 | A61K 9/20 |

OTHER PUBLICATIONS

Office action dated Oct. 26, 2007 issued in U.S. Appl. No. 10/901,898.
Office action dated Feb. 28, 2008 issued in U.S. Appl. No. 10/901,898.
Office action dated Oct. 20, 2008 issued in U.S. Appl. No. 10/901,898.
Office action dated Aug. 4, 2009 issued in U.S. Appl. No. 10/901,898.
Office action dated Jan. 20, 2010 issued in U.S. Appl. No. 10/901,898.
Office action dated Jul. 27, 2012 issued in U.S. Appl. No. 10/901,898.
Office action dated Jan. 17, 2013 issued in U.S. Appl. No. 10/901,898.

COMPOSITION COMPRISING A BENZIMIDAZOLE AND PROCESS FOR ITS MANUFACTURE

CROSS-REFERENCE TO RELATED APPLICATIONS

The present application is a continuation of pending U.S. application Ser. No. 10/901,898, filed 29 Jul. 2004. The above referenced application is incorporated herein by reference in its entirety.

FIELD OF THE INVENTION

The invention relates to a novel composition comprising a benzimidazole, said composition being notably free of any binder. The invention also relates to a very simple process for the manufacture of the present composition.

BACKGROUND OF THE INVENTION

Benzimidazoles are known proton pump inhibitors. Representatives of this class of drugs are omeprazole, esomeprazole, pantoprazole, rabeprazole. Many formulation patents are known for this type of active pharmaceutical ingredient. WO-A-9712581 discloses a composition exempt of alkaline-reacting compounds comprising:

(a) a core containing a benzimidazole active ingredient, said core being constituted of nuclei and said active ingredient mixed together and then compressed together, and said active ingredient not being in the form of an alkaline salt, and where a polymer acting as a binder is generally used in the core manufacture;

(b) an intermediate layer; and (c) an enteric layer applied onto the intermediate layer.

U.S. Pat. No. 5,997,903 discloses a medicament in pellet or tablet form which contains the active compound pantoprazole, which is to be administered orally, is resistant to gastric juice and consists of a basic pellet core or tablet core, one or more inert, water-soluble intermediate layer(s) and an outer layer which is resistant to gastric juice, and which is characterized in that the core contains, in addition to pantoprazole or in addition to a pantoprazole salt, polyvinylpyrrolidone and/or hydroxypropylmethylcellulose as the binder, and if desired mannitol additionally as an inert filler. US2003114494 discloses a stable oral pharmaceutical which comprises a benzimidazole, comprising:

(a) an inert core;

(b) thereon an active ingredient layer which comprises the benzimidazole mixed with an acidic reacting compound and, where appropriate, pharmaceutically acceptable adjuvants among which binders (water-soluble polymers) which are always used in this document;

(c) at least one inert layer; and (d) an enteric layer applied onto said at least one inert layer.

Albeit "tablet" is mentioned in this latter document, the tablet form is only mentioned and is not exemplified; this document is in fact essentially towards the pellet form.

There is still a need for a composition which can be either alkaline free or not, or even can contain an acidic compound, and which would be easy to manufacture, notably without having to revert to any binder. None of the above documents teaches or suggests the instant invention.

SUMMARY OF THE INVENTION

The invention provides new benzimidazole compositions, especially the following compositions:

A composition comprising a benzimidazole active ingredient, said composition comprising:
(a) a core containing said benzimidazole active ingredient;
(b) an intermediate layer; and
(c) an enteric layer;
said core being substantially free of binder; or said core being substantially free of PVP and of HPMC.

A composition comprising a benzimidazole active ingredient, said composition comprising:
(a) a core containing said benzimidazole active ingredient, where said core consists essentially of, by weight:
  about 10 to about 80 parts of said benzimidazole active ingredient,
  about 20 to about 85 parts of a first, water-soluble, diluent,
  about 0 to about 80 parts of a second, water-insoluble, diluent,
  about 10 to about 40 parts of a disintegrant; and
  0 to about 5 parts of a lubricant;
(b) an intermediate layer; and
(c) an enteric layer.

A composition comprising a benzimidazole active ingredient, said composition comprising:
(a) a core containing said benzimidazole active ingredient, where said core consists essentially of, by weight:
  about 15 to about 60 parts of said benzimidazole active ingredient,
  about 40 to about 75 parts of lactose,
  about 15 to about 30 parts of a disintegrant, and
  about 0.5 to about 5 parts of a lubricant;
(b) an intermediate layer; and
(c) an enteric layer.

A composition comprising a benzimidazole active ingredient not being in the form of an alkaline salt, said composition being exempt of alkaline-reacting compounds, said composition comprising:
(a) a core containing said benzimidazole active ingredient, where said core consists essentially of, by weight:
  about 15 to about 60 parts of said benzimidazole active ingredient,
  about 40 to about 75 parts of a first, water-soluble, diluent,
  about 0 to about 40 parts of a second, water-insoluble, diluent,
  about 15 to about 30 parts of a disintegrant, and
  about 0.5 to about 5 parts of a lubricant;
(b) an intermediate layer; and
(c) an enteric layer.

A composition comprising omeprazole or esomeprazole or pantoprazole or lansoprazole or rabeprazole, said composition comprising:
(a) a core containing said omeprazole or esomeprazole or pantoprazole or lansoprazole or rabeprazole, where said core consists essentially of, by weight:
  about 15 to about 60 parts of said omeprazole or esomeprazole or pantoprazole or lansoprazole or rabeprazole,
  about 40 to about 75 parts of lactose,
  about 15 to about 30 parts of a disintegrant, and
  about 0.5 to about 5 parts of a lubricant;
(b) an intermediate layer; and
(c) an enteric layer.

The invention also provides a process for manufacturing the compositions of the invention, said process comprising the steps of: (i) granulating said active ingredient with said diluents, said disintegrant and said lubricant if any; (ii) compressing the product of step (i) to form a tablet core containing an active ingredient; (iii) coating said core with said intermediate layer; and (iv) coating a product from step (iii) with said enteric layer.

DETAILED DESCRIPTION OF EMBODIMENTS OF THE INVENTION

The invention is designed for any benzimidazole, which is a class of compounds that is generally known. Here, the expression "benzimidazole active ingredient" should be taken to mean benzimidazole derivatives that are of therapeutic value. The benzimidazole active ingredients as used in the instant application are notably, but not limitatively, disclosed in the following patents and patent applications: EP-A-0,005, 129, EP-A-0,080,602, EP-A-0,127,763, EP-A-0,130,729, EP-A-0,134,400, EP-A-0,146,370, EP-A-0,150,586, EP-A-0,166,287, EP-A-0,173,664, EP-A-0,244,380, DE-3,415, 971, GB-A-2,082,580, GB-A-2,141,429, GB-A-2163747, U.S. Pat. No. 4,045,563, U.S. Pat. No. 4,182,766, U.S. Pat. No. 4,255,431, U.S. Pat. No. 4,337,257, U.S. Pat. No. 4,508, 905, U.S. Pat. No. 4,628,098, U.S. Pat. No. 4,689,333, U.S. Pat. No. 4,734,416, U.S. Pat. No. 4,738,974, U.S. Pat. No. 4,758,579, U.S. Pat. No. 4,786,505, U.S. Pat. No. 4,853,230, U.S. Pat. No. 5,006,528, U.S. Pat. No. 5,013,743, U.S. Pat. No. 5,026,560, U.S. Pat. No. 5,035,899, U.S. Pat. No. 5,039, 806, U.S. Pat. No. 5,045,321, U.S. Pat. No. 5,045,552, U.S. Pat. No. 5,093,132, U.S. Pat. No. 5,433,959, U.S. Pat. No. 5,690,960, U.S. Pat. No. 5,714,504, U.S. Pat. No. 5,877,192, U.S. Pat. No. 5,900,424, U.S. Pat. No. 5,997,903, U.S. Pat. No. 6,147,103, U.S. Pat. No. 6,150,380, U.S. Pat. No. 6,166, 213, U.S. Pat. No. 6,191,148, U.S. Pat. No. 6,369,085, and U.S. Pat. No. 6,428,810. The instant invention notably applies to omeprazole, esomeprazole, pantoprazole, lansoprazole, leminoprazole, pariprazole, rabeprazole, timoprazole, ariprazole and diapiprazole.

The alkaline salt form or derivative of the active ingredients cited above is also suitable in one embodiment. Derivatives, such as salts (hydrates such as sesquihydrates, etc.), alkaline salts (salts formed with lithium, sodium, magnesium, potassium, calcium etc. as well as any other base), esters and the like (including pro-drugs), are also contemplated. It is also possible to use an alkaline-reacting agent together with the benzimidazole active ingredient. Examples of such agents which may be mentioned here are the pharmacologically tolerated alkali metal, alkaline earth metal or earth metal salts of weak acids and the pharmacologically tolerated hydroxides and oxides of alkaline earth and earth metals, such as sodium carbonate, calcium carbonate, magnesium carbonate, magnesium oxide and magnesium hydroxide. Acidic reacting-agent such as those disclosed in US2003114494, notably sodium dihydrogen phosphate ($NaH_2PO_4$), can also be used.

Here, the expression "exempt of alkaline-reacting compound" should be taken to mean a composition that substantially does not contain any alkaline-reacting compound, in other words a composition in which the amount of alkaline-reacting compound is not sufficient to set up an alkaline micro-environment around the active ingredient when it is in contact with an acid or neutral aqueous medium, for example a micro-environment having a pH above 7. In one embodiment, said benzimidazole active ingredient is not in the form of an alkaline salt, and said composition is exempt of alkaline-reacting compounds. Mixtures of active ingredients are also envisaged, for example those comprising a benzimidazole in association with another active ingredient, or those containing two benzimidazoles.

The core contains the benzimidazole active ingredient together with various excipients, notably diluents (also known as fillers) and disintegrant, and optionally lubricant. The diluents will generally comprise a first diluent which is water-soluble, and optionally a second diluent which is water-insoluble (or hydrodispersible). These types of diluents are known in the art. They are crystalline or amorphous, and are generally inert with respect to the benzimidazole active ingredient.

Examples of the first water-soluble diluent are lactose, mannitol, and mixtures thereof. Lactose is preferred. Examples of the second water-insoluble diluent, if used, are cellulose acetate, microcrystalline cellulose, and mixtures thereof. Cellulose acetate is preferred. When the composition comprises a first diluent and a second diluent, the weight ratio first diluent to second diluent is preferably from about 1.5:1 to 1:1.5. The particle size of the first (and optionally second diluent) is not critical. In general, the $d_{50}$ of the diluent particle is from about 50 μm to about 400 μm, preferably from about 75 μm to about 150 μm.

The disintegrant can be any compound known in the art to that effect. Examples of disintegrants are cross-linked polyvinylpyrrolidone (crospovidone), sodium croscarmellose, sodium carboxymethyl starch, modified starch or unmodified starch, colloidal silica and mixtures thereof. The preferred disintegrant is cross-linked polyvinylpyrrolidone (crospovidone). The lubricant can be selected from the group consisting of sodium stearylfumarate, magnesium stearate, talc, glyceryl behenate and mixtures thereof.

These compounds are used in varying amounts. Exemplary amounts are:
about 10 to about 80 parts, preferably about 15 to about 60 parts of said benzimidazole active ingredient;
about 20 to about 85 parts, preferably about 40 to about 75 parts, of said first, water-soluble, diluent;
about 0 to about 80 parts, preferably about 0 to about 40 parts, of said second, water-insoluble, diluent, and most preferably no second, water-insoluble, diluent is used;
about 10 to about 40 parts, preferably about 15 to about 30 parts, of said disintegrant;
0 to about 5 parts, preferably about 0.5 to about 5 parts, of said lubricant.

One exemplary core formulation is one where said core consists essentially of, by weight:
about 15 to about 60 parts of said benzimidazole active ingredient,
about 40 to about 75 parts of lactose,
about 15 to about 30 parts of a disintegrant, and
about 0.5 to about 5 parts of a lubricant.

Another exemplary core formulation is one where said core consists essentially of, by weight:
about 15 to about 60 parts of said benzimidazole active ingredient,
about 30 to about 60 parts of lactose,
about 30 to about 60 parts of cellulose acetate,
about 15 to about 30 parts of a disintegrant, and about 0.5 to about 5 parts of a lubricant.

In one embodiment, the core consists essentially of the benzimidazole active ingredient, of the first, water-soluble diluent, optionally of the second, water-insoluble, diluent, of the disintegrant, and optionally of the lubricant. In another, preferred embodiment, the core consists essentially of the benzimidazole active ingredient, of the first, water-soluble diluent, the disintegrant, and the lubricant. The term "consisting essentially of", in one embodiment, is intended to mean that the listed compounds represent more than 90% by weight of the core, preferably more than 95% by weight of the core, most preferably more than 98% by weight of the core.

Other excipients such as fillers, plastifiers, surfactants, pigments, wetting agents, etc. may also be present in the core or the additional layers, if need be. The excipients can be any one traditionally used in the art. For more details about these excipients, one can refer to the disclosure in "Handbook of pharmaceutical excipients", American Pharmaceutical Association, 1994 ISBN 0 91730 66 8, by Wade A. and Weller P. Examples are polysorbate 80, sodium lauryl sulfate, colloidal silica, titanium dioxide, etc.

The intermediate layer, according to the invention comprises of at least one sub-layer. It corresponds to one or several inert water-soluble layers or layers which rapidly disintegrate in an aqueous medium, containing inert pharmaceutical excipients. This layer comprises at least one polymer conventionally used in applications where a film is provided by coating such as: sugars, polyethyleneglycol, polyvinylpyrrolidone, poly(vinyl alcohol), hydroxypropylcellulose, hydroxymethylcellulose, hydroxypropylmethylcellulose, gelatine, etc. This intermediate layer is applied to the core using any coating technique conventionally employed in a suitable coating tank or in a fluidized bed device, with the use of suitable aqueous and/or organic solvents, or by using latex suspensions of said excipients. Water is the preferred solvent. Examples which may be mentioned of film-forming polymers (generally water-soluble polymers albeit water-insoluble polymers may be used) which can be used advantageously for the intermediate layer are given above, and especially hydroxypropylmethylcellulose and/or polyvinylpyrrolidone, to which plasticizers (such as, for example, propylene glycol) and/or other additives and auxiliaries (e.g. buffers, bases, pigments, surfactants, etc.) can also be added if desired. These other additives and auxiliaries or excipients can be any one of the conventional pharmaceutical excipients cited in the section relating to the core, or a mixture thereof. Talc is one preferred excipient used in the intermediate layer.

An exemplary composition for the intermediate layer comprises by weight, based on the weight of said layer:
about 30% to about 80%, preferably about 50% to about 70%, of hydroxypropylmethylcellulose (or another polymer such as PVP);
about 15% to about 50%, preferably about 20% to about 40%, of talc;
about 3% to about 25%, preferably about 5% to about 15%, of titanium dioxide.

The enteric layer according to this invention corresponds to at least one sub-layer that is entero-soluble and gastro-resistant. It is applied to the intermediate layer by conventional coating techniques such as coating in a tank or a fluidized bed employing polymer solutions in water or in suitable organic solvents or using latex suspensions of these polymers. Water is the preferred solvent. The enteric coating can also be applied using aqueous dispersions of polymers. Water-soluble or water-insoluble polymers, or mixtures thereof can be used, according to methods known in the art. The expert knows, on the basis of his technical knowledge, what outer layers which are resistant to gastric juice can be used.

As a polymer, use can be made of: cellulose phthalates and derivatives thereof, cellulose acetyl phthalate, hydroxypropyl-methylcellulose phthalate, polyvinyl phthalate acetate, as well as (meth)acrylic (co)polymers. As acrylic copolymers, one may cite especially the methacrylic acid/alkyl (meth) acrylate copolymers (sold as Eudragit®). A methyl radical and an ethyl radical are preferred as alkyl radical. The methacrylic acid type C copolymer complying with the US pharmacopoeia is one polymer suited. A preferred polymer is a copolymer based on methacrylic acid and ethyl acrylate, in which the ratio of free carboxyl groups to esters groups is about 1:1. The average molecular weight is, for example, about 250,000. Exemplary coating polymers are commercially available; they are those available as Aquateric® (FMC Corporation), CE5142 coating (BASF) and especially the Eudragit® products (Rohm Pharma), these latter being preferred.

The enteric layer can also contain a pharmaceutically-acceptable plastifying agent such as, for example, ketanol, triacetine, citric acid esters (e.g. triethyl citrate) such as those known under as Citroflex® (Pfizer), phthalic acid esters, dibutylsuccinate, polyethyleneglycol of varying molecular weights, or any other similar plastifying agent. The amount of plastifying agent is in general optimized for each polymer and the plastifying agent generally represents by weight 1 to 30% of the polymer, for example from 5 to 25%. Supplementary agents such as talc, pigments, coloring agents, flavoring agents, as well as any other excipient that conventionally enters into the composition of enteric coatings can be employed; such other conventional excipients being e.g. those disclosed in connection with the core. Talc is one preferred excipient.

An exemplary composition for the enteric layer comprises by weight, based on the weight of said layer:
about 50% to about 90%, preferably about 60% to about 85%, of methacrylic acid/alkyl (meth)acrylate copolymer (or another enteric polymer);
about 3% to about 25%, preferably about 5% to about 15%, of triethyl citrate (or another plastifying agent);
about 5% to about 30%, preferably about 10% to about 20%, of talc.

The composition according to the present invention generally comprises, based on the total weight of the composition:
a core representing about 70 to about 95% by weight, preferably about 70 to about 90% by weight;
an intermediate layer representing about 5 to about 30% by weight, preferably about 8 to about 15% by weight;
an enteric layer representing from about 3 to about 20% by weight, preferably about 5 to about 15% by weight.

It should be noted that additional layers or sub-layers can be added, for the purposes of adding flavor and/or color, and/or improving acceptability of the medicament and/or allowing it to be marked.

The process used to manufacture the instant composition is very simple. First a core is manufactured, and then the intermediate and enteric layers are coated on said core using any classical method. The present invention brings a novel manufacturing process as far as the core is concerned. It is important to note that the present process allows manufacturing the core without recourse to any binder.

The core is generally manufactured as follows. In a first step, the various ingredients are granulated together. In a second step, a tablet is obtained starting from the granulates obtained at the first step by compressing the product.

The first granulating step can be carried out by using any granulating method, such as dry granulation, sieving, fluidized bed granulation or wet granulation. In the case of fluidized bed granulation and wet granulation, one uses suitable aqueous and/or organic solvents, preferably an aqueous solvent. Wet granulation is the preferred method. The apparatus that can be used is for example a high shear mixer. It should be noted that the disintegrant used in the composition can be partly into the granulate and partly in the outer phase. The weight ratio distribution granulate:outer phase of the disintegrant can be from 100:0 to 0:100, especially 70:30 to 0:100.

In one preferred embodiment, the process for manufacturing the core comprises the following sub-steps:
- (a) dry mixing said benzimidazole active ingredient, said first diluent and optionally said second diluent and optionally part of said disintegrant;
- (b) granulating the product of sub-step (a) with water;
- (c) drying the granulates of sub-step (b); and
- (d) dry mixing the dried granulates of sub-step (c) with said disintegrant or the remainder thereof and said lubricant.

The drying step can be carried out in any conventional apparatus known to that effect, for example a fluidized bed or a drying oven. The drying step is considered as having been carried out when the residual water content is below 10%, for example below 3%, depending on the kind and amount of ingredients. Tableting then follows granulation. The tableting step can be implemented using any conventional technique which is suitable, for example using alternating or rotating compressing equipment. In another, less preferred, embodiment, the core can be obtained by direct, dry, compression.

The water, if used, needed to produce the core is generally present in an amount of from 10% to 100% of the core weight. The water needed to produce the intermediate layer and/or the enteric layer is generally present in an amount of from 100% to 1000% of the intermediate and/or enteric layer weight.

In one preferred embodiment, the composition according to the invention is provided in a single tablet form (which may be breakable, if need be). In another embodiment, the composition is in the form of micro-tablets enclosed inside a capsule, e.g. a gelatin capsule. For this, any gelatin capsule conventionally employed in the pharmaceutical formulation field can be used, such as the hard gelatin capsule known as Capsugel®, available from Eli Lilly. The compositions of this invention are particularly suitable for oral administration of the active ingredients and are particularly suitable for treating gastro-intestinal sicknesses.

EXAMPLES

The following examples illustrate the invention without limiting it.

Example 1

The following core formulations are prepared.

|  | Amount (mg/unit) | |
| --- | --- | --- |
| Compound | Ex. 1A | Ex. 1B |
| Rabeprazole Na | 20.10 | — |
| Pantoprazole Na Sesquihydrate | — | 45.10 |
| Lactose 200mesh | 44.00 | 44.00 |
| Cellulose Acetate | 44.00 | 44.00 |
| Glyceryl behenate | 1.50 | 1.50 |
| Crospovidone | 22.40 | 22.40 |
| Water* | 40.00 | 40.00 |
| Total (dry) | 131.90 | 157.00 |

*evaporates off during process

Active ingredient, lactose and cellulose acetate are dry mixed. Water is added and granulation is carried out in a gravity funnel. Granulates are dried at 55° C. for 45 minutes. Crospovidone and glyceryl behenate are then added and mixed. The resulting mixture is then compressed into tablets (using a BetaPress® from Manesty with a punch having a curvature and a diameter of 7 mm—also known as 7R7).

The following intermediate layer formulation is used.

| Compound | Amount (mg/unit) |
| --- | --- |
| HPMC 3 cp | 11.75 |
| Titanium dioxide | 2.35 |
| Talc | 5.90 |
| Water* | 100 |
| Total | 20.00 |

*evaporates off during process

HPMC is dissolved in the water, and talc and titanium dioxide are then added. The suspension is homogenized and sprayed onto the tableted core in a coating pan (vector corporation perforated pan coater type LDCS).

The following enteric coating layer formulation is used.

| Compound | Amount (mg/unit) |
| --- | --- |
| Eudragit ® L30D | 11.10 |
| Talc | 2.23 |
| Triethyl citrate | 1.67 |
| Water* | 44 |
| Total | 15.00 |

*evaporates off during process

Triethyl citrate is dissolved in 60% of the water. The resulting solution is added to the Eudragit polymer and let in contact for 45 minutes under low stifling. Talc is added to the remaining 40% water, and the suspension is homogenized. Both compositions are then combined into one solution which is sprayed onto the intermediate coated core in a coating pan (identical to the one used for the intermediate layer) using a peristaltic pump and a spray nozzle (available from company spray systems).

Example 2

The following core formulations are prepared.

|  | Amount (mg/unit) | |
| --- | --- | --- |
| Compound | Ex. 2A | Ex. 2B |
| Rabeprazole Na | 20.00 | — |
| Pantoprazole Na Sesquihydrate | — | 45.10 |
| Lactose 200mesh | 88.00 | 88.00 |
| Glyceryl behenate | 1.50 | 3.00 |
| Crospovidone | 22.00 | 22.90 |
| Water* | 40.00 | 20.00 |
| Total (dry) | 131.50 | 159.00 |

*evaporates off during process

For example 2A, the process is as in example 1. For example 2B, the process differs in that half of crospovidone is mixed to form the granulates and half is mixed with the granulates as in example 1. The intermediate and enteric layers are as in example 1 and the process for coating is the same.

What is claimed is:

1. A pharmaceutical composition comprising:
   (a) a core that is free of binder;
   (b) an intermediate layer; and
   (c) an enteric layer; wherein the core consists essentially of, by weight:
   about 15 to about 60 parts of pantoprazole sodium,
   about 30 to about 60 parts of lactose,
   about 30 to about 60 parts of cellulose acetate,
   about 15 to about 30 parts of a disintegrant, and
   about 0.5 to about 5 parts of a lubricant and wherein the lactose and the cellulose acetate are present in a weight ratio of about 1.5:1 to 1:1.5.

2. The composition of claim 1, wherein the disintegrant comprises cross-linked polyvinylpyrrolidone.

3. The composition of claim 1, provided either in a single tablet form or in the form of micro-tablets enclosed inside a capsule.

4. The composition of claim 1, wherein the lubricant comprises sodium stearylfumarate, magnesium stearate, talc, glyceryl behenate or a mixture thereof.

5. The composition of claim 1, wherein the core further comprises a filler, plastifier, surfactant, pigment, wetting agent, or mixture thereof.

6. The composition of claim 1, wherein the core additionally comprises at least one further excipient that is other than a binder.

7. The composition of claim 1, wherein the sodium salt of pantoprazole comprises pantoprazole sodium sesquihydrate.

* * * * *